United States Patent
Park et al.

(10) Patent No.: US 9,783,557 B2
(45) Date of Patent: Oct. 10, 2017

(54) METALLOCENE CATALYST FOR PREPARING A HIGH MOLECULAR WEIGHT POLYOLEFIN AND A PREPARATION METHOD THEREOF

(71) Applicant: LG CHEM, LTD., Seoul (KR)

(72) Inventors: Hee Kwang Park, Daejeon (KR); Byung Seok Kim, Daejeon (KR); Hye Kyung Lee, Daejeon (KR); Jae Youp Cheong, Daejeon (KR); Kyung Seop Noh, Daejeon (KR); Sang Eun An, Daejeon (KR); In Sun Lee, Daejeon (KR); Sang Jin Jeon, Daejeon (KR)

(73) Assignee: LG CHEM, LTD., Seoul (KR)

(*) Notice: Subject to any disclaimer, the term of this patent is extended or adjusted under 35 U.S.C. 154(b) by 0 days.

(21) Appl. No.: 14/910,929

(22) PCT Filed: Oct. 8, 2015

(86) PCT No.: PCT/KR2015/010681
§ 371 (c)(1),
(2) Date: Feb. 8, 2016

(87) PCT Pub. No.: WO2016/060412
PCT Pub. Date: Apr. 21, 2016

(65) Prior Publication Data
US 2016/0257703 A1    Sep. 8, 2016

(30) Foreign Application Priority Data
Oct. 17, 2014  (KR) .................. 10-2014-0140956

(51) Int. Cl.
| | | |
|---|---|---|
| C07F 17/00 | (2006.01) | |
| C08F 4/6592 | (2006.01) | |
| C08F 10/00 | (2006.01) | |
| C07F 7/08 | (2006.01) | |
| C08F 110/06 | (2006.01) | |
| C08F 210/06 | (2006.01) | |
| C08F 4/659 | (2006.01) | |

(52) U.S. Cl.
CPC .......... *C07F 7/082* (2013.01); *C08F 4/65927* (2013.01); *C08F 110/06* (2013.01); *C08F 210/06* (2013.01); *C08F 4/65912* (2013.01); *C08F 4/65916* (2013.01)

(58) Field of Classification Search
CPC .. C08F 4/65927; C08F 4/65912; C08F 10/00; C07F 17/00
See application file for complete search history.

(56) References Cited

U.S. PATENT DOCUMENTS

| | | |
|---|---|---|
| 7,671,223 B2 | 3/2010 | Garcia et al. |
| 2004/0171855 A1 | 9/2004 | Fritze et al. |
| 2006/0116490 A1 | 6/2006 | Paczkowski et al. |
| 2008/0287286 A1 | 11/2008 | Paczkowski et al. |
| 2010/0261860 A1 | 10/2010 | Schulte et al. |
| 2015/0031844 A1 | 1/2015 | Lee et al. |
| 2015/0073107 A1 | 3/2015 | Choi et al. |

FOREIGN PATENT DOCUMENTS

| | | |
|---|---|---|
| CN | 1950384 A | 4/2007 |
| EP | 1077215 B1 | 2/2004 |
| EP | 1807456 B1 | 7/2012 |
| EP | 3078681 A1 | 10/2016 |
| JP | 2000-095791 A | 4/2000 |
| JP | 2014-505136 A | 2/2014 |
| JP | 5551334 B2 | 7/2014 |
| KR | 10-2013-0049148 A | 5/2013 |
| KR | 10-1278336 B1 | 6/2013 |
| KR | 10-2013-0113322 A | 10/2013 |
| KR | 10-2013-0125311 A | 11/2013 |
| KR | 10-1354477 B1 | 1/2014 |
| KR | 10-1437509 B1 | 9/2014 |
| KR | 10-2014-0133343 A | 11/2014 |
| KR | 10-2015-0037631 A | 4/2015 |
| WO | 2004/041871 A1 | 5/2004 |
| WO | 2005/052011 A1 | 6/2005 |
| WO | 2013/066109 A1 | 5/2013 |
| WO | 2013/168928 A1 | 11/2013 |

OTHER PUBLICATIONS

V. Izmer, et al.: "Palladium-Catalyzed Pathways to Aryl-Substituted Indenes: Efficient Synthesis of Ligands and the Respective ansa-Zirconocenes", Organometallics 2006, vol. 25, Nov. 1, 2015, pp. 1217-1229.
Y. Nakayama, et al.: "Developments of Chiral Metallocenes as Polymerization Catalysts", Molecules 2005, vol. 10, Jul. 14, 2005, pp. 620-633.
I. Nifant'Ev, et al.: "5-Methoxy-Substituted Zirconium Bis-indenyl ansa-Complexes: Synthesis, Structure, and Catalytic Activity in the Polymerization and Copolymerization of Alkenes", XP055060553, Organometallics 2012, vol. 31, No. 14, Jul. 23, 2012, pp. 4962-4970.

*Primary Examiner* — Caixia Lu
(74) *Attorney, Agent, or Firm* — Dentons US LLP

(57) ABSTRACT

The present invention relates to a metallocene compound having novel structure which can provide various selectivity and activity to polyolefin copolymers, a preparation method thereof, and a preparation method of polyolefin using the metallocene compound.

5 Claims, No Drawings

METALLOCENE CATALYST FOR PREPARING A HIGH MOLECULAR WEIGHT POLYOLEFIN AND A PREPARATION METHOD THEREOF

CROSS-REFERENCE TO RELATED APPLICATION(S)

This application is a National Phase entry of PCT/KR2015/010681 filed on Oct. 8, 2015 and claims priority to Korean Application No. 10-2014-0140956 filed Oct. 17, 2014, both of which are incorporated by reference for all purposes as if fully set forth herein.

TECHNICAL FIELD

The present invention relates to a metallocene catalyst having novel structure for preparing a high molecular weight polyolefin.

BACKGROUND OF THE INVENTION

The catalyst for olefin polymerization may be classified into Zeigler-Natta catalyst system and metallocene catalyst system, and these two highly active catalyst systems have been respectively developed according to their characteristics. Zeigler-Nana catalyst had been widely used in prior commercial processes since it was invented in 1950's, but it was characterized in that the molecular weight distribution of the polymers obtained by using the same was wide because it is a multi-site catalyst having a plurality of active sites and thus there was a problem of that the composition distribution of the comonomers in the polymer was not even and there was a limitation in securing the properties required.

Metallocene catalyst consists of a combination of a main catalyst in which a transition metal compound is a main component and an organometal compound, a cocatalyst, in which aluminum is a main component. Such catalyst is a homogeneous complex catalyst and a single site catalyst. The polymer of which the molecular weight distribution is narrow and the composition distribution of the comonomers is even can be obtained by using the same due to the single site characteristic, and the stereoregularity, the copolymerization characteristics, the molecular weight, the crystallinity, and so on of the polymer can be changed by varying the ligand structure of the catalyst and the polymerization conditions.

Meanwhile, an ansa-metallocene compound is an organometal compound having two ligands which are connected by a bridge group, wherein the rotation of the ligands is prevented and the activity and the structure of the metal center are determined by the bridge group.

Such ansa-metallocene compound is being used as a catalyst for preparing an olefinic homopolymer or copolymer. Particularly, it is known that a high molecular weight polyethylene can be prepared and the microstructure of a polypropylene can be controlled by using the ansa-metallocene compound including a cyclopentadienyl-fluorenyl ligand. Furthermore, it is known that the ansa-metallocene compound having an indenyl ligand has excellent activity and can be used to prepare a polyolefin having an enhanced stereoregularity.

The present inventors have disclosed an ansa-metallocene compound of novel structure which can provide various selectivity and activity to polyolefin copolymers in Korean Patent Publication No. 10-2013-0125311.

Meanwhile, when the ansa-metallocene catalyst has bis-indenyl ligand, two types of isomer, namely, a racemate and a mirror-symmetric meso diastereomer, may be formed according to steric arrangement of two ligands. The racemate is preferred because it is used to prepare an isotactic polymer having high crystallinity and melting point and large specific gravity and mechanical strength, but the mirror-symmetric meso diastereomer is avoided because it prepares an atactic polymer. However, the racemate and the mirror-symmetric meso diastereomer are simultaneously prepared in the preparation process of the ansa-metallocene catalyst, and thus the structure of the ansa-metallocene catalyst in which an excess of the racemate can be formed must be importantly considered.

Therefore, the present inventors have conducted various studies on the ansa-metallocene catalyst that has higher activity than prior known catalysts and can control the microstructure of olefin polymer, and accomplished the present invention by recognizing that the metallocene catalyst having the structure of the present invention disclosed in this specification satisfies above characteristics.

DETAILS OF THE INVENTION

Objects of the Invention

An objective of the present invention is to provide a metallocene compound having novel structure that has high activity and can control the microstructure of olefin polymer.

Another objective of the present invention is to provide a preparation method of the metallocene compound having novel structure.

Another objective of the present invention is to provide a catalyst for olefin polymerization comprising the metallocene compound having novel structure.

Another objective of the present invention is to provide a preparation method of a polyolefin using the metallocene compound having novel structure.

Means for Achieving the Object

To resolve the problems disclosed above, the present invention provides a compound represented by following Chemical Formula 1:

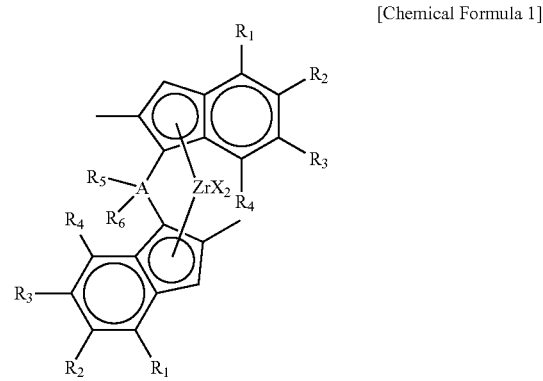

[Chemical Formula 1]

in above Chemical Formula 1,
X is halogen, same to or different from each other,
$R_1$ is $C_{6-20}$ aryl substituted with $C_{1-20}$ alkyl,
$R_2$, $R_3$ and $R_4$ are independently hydrogen, halogen, $C_{1-20}$ alkyl, $C_{2-20}$ alkenyl, $C_{1-20}$ alkylsilyl, $C_{1-20}$ silylalkyl, $C_{1-20}$ alkoxysilyl, $C_{1-20}$ ether, $C_{1-20}$ silylether, $C_{1-20}$ alkoxy, $C_{6-20}$ aryl, $C_{7-20}$ alkylaryl, or $C_{7-20}$ arylalkyl,
A is carbon, silicon, or germanium,
$R_5$ is $C_{1-20}$ alkyl substituted with $C_{1-20}$ alkoxy, and
$R_6$ is hydrogen, $C_{1-20}$ alkyl, or $C_{2-20}$ alkenyl.

The compound represented by Chemical Formula 1 has an ansa-metallocene structure, and comprises two indenyl groups as ligands. Specifically, it has an advantage in that the activity of the catalyst can be maximized because the bridge group connecting the ligands is substituted with the functional group which can take a role of Lewis base as an oxygen-donor. Furthermore, since the indenyl groups are substituted by a bulky group such as $C_{6-20}$ aryl substituted with $C_{1-20}$ alkyl ($R_1$), a steric hindrance occurs and the formation of meso-form is prevented. Therefore, the compound represented by Chemical Formula 1 can be used to prepare a polyolefin having desired properties more easily when it is used as a catalyst for preparing the polyolefin by itself or in a supported form.

Preferably, X is chloro.

Preferably, $R_1$ is phenyl substituted with tert-butyl. More preferably, $R_1$ is 4-tert-butyl-phenyl.

Preferably, $R_2$, $R_3$ and $R_4$ are hydrogen.

Preferably, A is silicon.

Preferably, $R_5$ is 6-tert-butoxy-hexyl, and $R_6$ is methyl.

The representative example of the compound of Chemical Formula 1 is as follows:

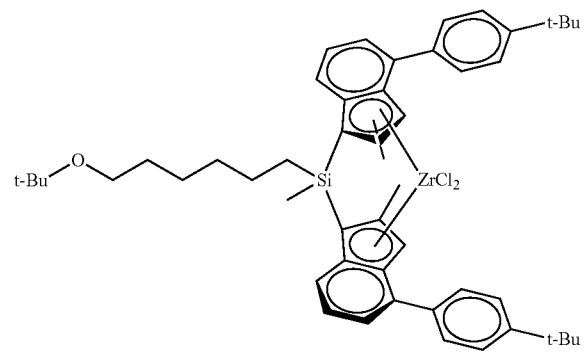

The present invention also provides a preparation method of the compound represented by Chemical Formula 1, according to the following Reaction Formula 1:

[Reaction Formula 1]

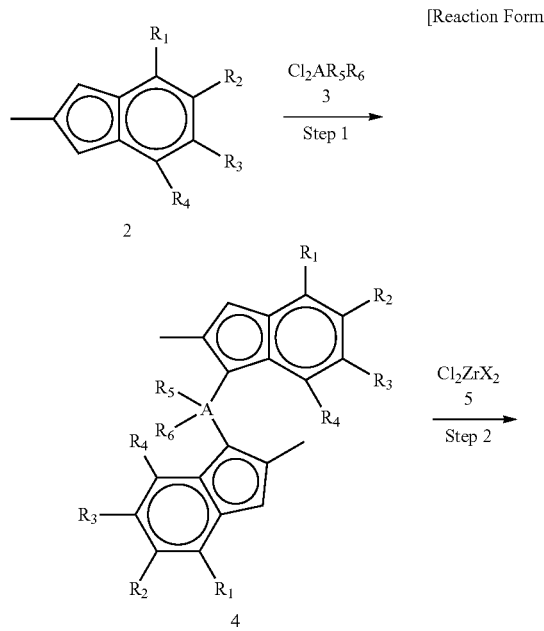

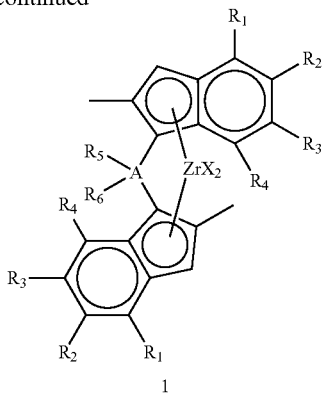

The step 1 is the step of preparing the compound represented by Chemical Formula 4 by reacting the compound represented by Chemical Formula 2 with the compound represented by Chemical Formula 3. It is preferable to use an alkyllithium (for example, n-butyllithium) in the reaction, and the reaction temperature is −200 to 0° C., or preferably −150 to 0° C. Toluene, THF, and the like may be used as the solvent. At this time, the steps of separating an organic layer from the product, vacuum drying the separated organic layer, and eliminating an excess of the reactant therefrom may be further carried out.

The step 2 is the step of preparing the compound represented by Chemical Formula 1 by reacting the compound represented by Chemical Formula 4 with the compound represented by Chemical Formula 5. It is preferable to use an alkyllithium (for example, n-butyllithium) in the reaction, and the reaction temperature is −200 to 0° C., or preferably −150 to 0° C. Ether, hexane, and the like may be used as the solvent.

The present invention also provides a catalyst for olefin polymerization comprising the compound represented by Chemical Formula 1. The compound represented by Chemical Formula 1 can be used as the catalyst for olefin polymerization by itself or in combination of a cocatalyst as a catalyst precursor.

The catalyst for olefin polymerization may be a catalyst supported on a carrier. The carrier is not limited particularly in the present invention if it is common in the related art but one or more carriers selected from the group consisting of silica, silica-alumina and silica-magnesia may be used preferably. Meanwhile, when the catalyst is supported on a carrier like silica, the silica carrier and the functional group of the compound represented by Chemical Formula 1 are chemically bonded. Therefore, the catalyst is hardly released from the surface during the olefin polymerization, and there is no fouling that is the adhesion of polymer onto a reactor wall or between polymer particles when the polyolefin is prepared by a slurry or vapor phase polymerization.

Further, the polyolefin prepared in the presence of the catalyst including such silica carrier is superior in the particle shape of polymer and the apparent density, and can be properly used to traditional slurry or vapor phase polymerization. Therefore, a carrier that is dried at high temperature and has siloxane groups having high reactivity may be used.

Specifically, silica, silica-alumina, and the like dried at high temperature may be used, and they may include an oxide, a carbonate, a sulfate or a nitrate component, such as $Na_2O$, $K_2CO_3$, $BaSO_4$, $Mg(NO_3)_2$, and so on.

Furthermore, the catalyst for olefin polymerization may further comprise a cocatalyst consisting of an alkylaluminoxane. When the cocatalyst is used, the catalyst may be used in the form of that X group bonded to the metal element of the compound represented by Chemical Formula 1 is substituted with an alkyl group, for example, $C_{1-20}$ alkyl.

The cocatalyst is also not limited particularly in the present invention because it is common in the related art but one or more cocatalysts selected from the group consisting of silica, silica-alumina, and an organoaluminum compound.

The present invention also provides a preparation method of a polyolefin, comprising the step of polymerizing at least one olefinic monomer in the presence of the catalyst for olefin polymerization. The olefinic monomer may be one or more monomers selected from the group consisting of ethylene, propylene, 1-butene, 1-pentene, 1-hexene, 4-methyl-1-pentene, 1-octene, 1-decene, 1-dodecene, 1-tetradecene, 1-hexadecene, 1-octadecene, 1-eicosene, and a mixture thereof.

Here, the polymerization reaction of the polyolefin may be carried out under the temperature of 25 to 500° C. and the pressure of 1 to 100 kgf/cm² for 1 to 24 hrs. At this time, the polymerization reaction temperature is preferably 25 to 200° C. and more preferably 50 to 100° C. Further, the polymerization reaction pressure is preferably 1 to 70 kgf/cm² and more preferably 5 to 40 kgf/cm². The polymerization reaction time is preferably 1 to 5 hrs.

The polymerization process can control the molecular weight range of the final polymer product according to whether hydrogen is added thereto or not. Particularly, the polyolefin of high molecular weight can be prepared when hydrogen is not added thereto, and the polyolefin of low molecular weight can be prepared even by adding a small quantity of hydrogen when hydrogen is added thereto. At this time, the amount of hydrogen added to the polymerization process may be 0.07 L to 4 L under the reactor condition of 1 atm, or hydrogen may be provided to the reactor with the pressure of 1 to 40 bar, or the mole ratio of hydrogen to olefinic monomer may be 168 to 8,000 ppm.

The polyolefin prepared by using the compound represented by Chemical Formula 1 according to the present invention as a catalyst can have higher molecular weight than when a traditional metallocene catalyst is used.

Effects of the Invention

The metallocene compound having novel structure according to the present invention is superior in catalytic activity to traditional metallocene compounds, and, when it is used as a catalyst itself or a catalyst precursor for preparing a polyolefin, the microstructure of the polymer can be easily controlled and particularly a polyolefin having high molecular weight property of low MI can be easily prepared.

DETAILED DESCRIPTION OF THE EMBODIMENT

Hereinafter, the present invention provides preferable examples for illuminating the present invention. However, following examples are only for understanding the present invention, and the range of the present invention is not limited to or by them.

Example

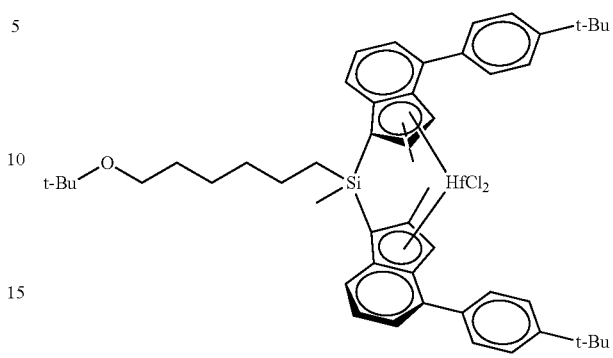

Step 1) Preparation of (6-t-butoxyhexyl)(methyl)-bis(2-methyl-4-tert-butyl-phenylindenyl)silane After dissolving 2-methyl-4-tert-butylphenylindene (20.0 g, 76 mmol) in toluene/THF=10/1 solution (230 mL), n-butyllithium solution (2.5 M, hexane solvent, 22 g) was slowly added thereto in drops at 0° C. and the mixture was stirred for a day at room temperature. And then, (6-t-butoxyhexyl)dichloromethylsilane (1.27 g) was slowly added to the mixture solution in drops at −78° C., and the mixture was stirred for 10 mins and further stirred at room temperature for a day. After separating the organic layer therefrom by adding water thereto, (6-t-butoxyhexyl)(methyl)-bis(2-methyl-4-tert-butyl-phenylindenyl)silane was obtained by distilling the solvent under a reduced pressure.

$^1$H NMR (500 MHz, CDCl$_3$, 7.26 ppm): −0.20-0.03 (3H, m), 1.26 (9H, s), 0.50-1.20 (4H, m), 1.20-1.31 (11H, m), 1.40-1.62 (20H, m), 2.19-2.23 (6H, m), 3.30-3.34 (2H, m), 3.73-3.83 (2H, m), 6.89-6.91 (2H, m), 7.19-7.61 (14H, m)

Step 2) Preparation of [(6-t-butoxyhexylmethylsilane-diyl)-bis(2-methyl-4-tert-butylphenylindenyl)] zirconium Dichloride After dissolving (6-t-butoxyhexyl)(methyl)-bis(2-methyl-4-tert-butyl-phenylindenyl)silane prepared in Step 1 in toluene/THF=5/1 solution (95 mL), n-butyllithium solution (2.5 M, hexane solvent, 22 g) was slowly added thereto in drops at −78° C. and the mixture was stirred for a day at room temperature. After dissolving bis(N,N-diphenyl-1,3-propanediamido)dichlorozirconium bis(tetrahydrofuran) [Zr(C$_5$H$_6$NCH$_2$CH$_2$NC$_5$H$_6$)Cl$_2$(C$_4$H$_8$O)$_2$] in toluene (229 mL), it was slowly added to above reacted solution in drops at −78° C. and the mixture was stirred for a day at room temperature. After cooling the reacted solution to −78° C., HCl ether solution (1 M, 183 mL) was slowly added thereto in drops and the mixture was stirred for 1 hr at 0° C. The solution was filtered and vacuum dried, and then the crystal was precipitated by adding hexane thereto and stirring the same. [(6-t-butoxyhexylmethylsilane-diyl)-bis(2-methyl-4-tert-butylphenylindenyl)]zirconium dichloride (20.5 g, total 61%) was obtained by filtering the precipitated crystal and drying the same under a reduced pressure.

$^1$H NMR (500 MHz, CDCl$_3$, 7.26 ppm): 1.20 (9H, s), 1.27 (3H, s), 1.34 (18H, s), 1.20-1.90 (10H, m), 2.25 (3H, s), 2.26 (3H, s), 3.38 (2H, t), 7.00 (2H, s), 7.09-7.13 (2H, m), 7.38 (2H, d), 7.45 (4H, d), 7.58 (4H, d), 7.59 (2H, d), 7.65 (2H, d)

Step 3) Preparation of a Supported Catalyst

After weighing 3 g of silica in a schlenk flask, 52 mmol of methylaluminoxane (MAO) was added thereto and the mixture was reacted at 90° C. for 24 hrs. After precipitation, the upper part was eliminated and the rest was washed twice with toluene. After dissolving 180 μmol of [(6-t-butoxyhexylmethylsilane-diyl)-bis(2-methyl-4-tert-butylphenylindenyl)]zirconium dichloride, the ansa-metallocene compound synthesized in above step, in toluene, the mixture was reacted at 70° C. for 5 hrs. When the precipitation was finished after the reaction, the solution of upper part was eliminated and the left reaction product was washed with toluene and washed with hexane again. After vacuum drying the washed product, 5 g of solid type metallocene catalyst supported on silica was obtained.

Comparative Example

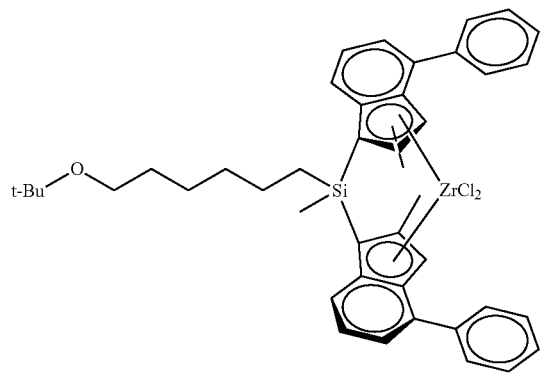

Step 1) Preparation of (6-t-butoxyhexyl)(methyl)-bis(2-methyl-4-phenylindenyl)silane After slowly adding 100 mL of t-butoxyhexyl magnesium chloride solution (about 0.14 mol, ether) to 100 mL of trichloromethylsilane solution (about 0.21 mol, hexane) in drops at −100° C. for 3 hrs, the mixture was stirred at room temperature for 3 hrs. After separating the transparent organic layer from the mixture solution, the transparent liquid phase of (6-t-butoxyhexyl)dichloromethylsilane was obtained by vacuum drying the separated transparent organic layer for eliminating an excess quantity of trichloromethylsilane.

15.4 mL of n-butyllithium solution (2.5 M, hexane solvent) was slowly added to 77 mL of 2-methyl-4-phenylindene toluene/THF=10/1 solution (34.9 mmol) in drops at 0° C., and the mixture solution was stirred at 80° C. for 1 hr and further stirred at room temperature for a day. After then, 5 g of (6-tert-butoxyhexyl)dichloromethylsilane prepared above was slowly added to the mixture solution in drops at −78° C., and the mixture was stirred for about 10 mins and further stirred at 80° C. for 1 hr. After separating the organic layer therefrom by adding water thereto, the sticky yellow oil (racemic:meso=1:1) was obtained with the yield of 78% by refining the product with a silica column and vacuum drying the same.

$^1$H NMR (500 MHz, CDCl$_3$, 7.24 ppm): 0.10 (3H, s), 0.98 (2H, t), 1.25 (9H, s), 1.36~1.50 (8H, m), 1.62 (8H, m), 2.26 (6H, s), 3.34 (2H, t), 3.81 (2H, s), 6.87 (2H, s), 7.25 (2H, t), 7.35 (2H, t), 7.45 (4H, d), 7.53 (4H, t), 7.61 (4H, d)

Step 2) Preparation of [(6-t-butoxyhexylmethylsilane-diyl)-bis(2-methyl-4-phenylindenyl)]zirconium Dichloride 3.0 mL of n-butyllithium solution (2.5 M in hexane) was slowly added to 50 mL of (6-tert-butoxyhexyl)(methyl)-bis(2-methyl-4-phenyl)indenylsilane ether/hexane=1/1 solution (3.37 mmol) prepared above in drops at −78° C., the mixture was stirred at room temperature for about 2 hrs and vacuum dried. The yellow solid was obtained by washing the salt with hexane and filtering and vacuum drying the same. After weighing the synthesized ligand salt and bis(N, N-diphenyl-1,3-propanediamido)dichlorozirconium bis(tetrahydrofuran) [Zr(C$_5$H$_6$NCH$_2$CH$_2$CH$_2$NC$_5$H$_6$)Cl$_2$(C$_4$H$_8$O)$_2$] in a glove box, ether was slowly added thereto in drops at −78° C. and the mixture was stirred at room temperature for a day. After then, the red reaction solution was filtered and separated therefrom, and 4 equivalents of HCl ether solution (1 M) was slowly added thereto in drops at −78° C. and the mixture was stirred for 3 hrs. And then, the ansa-metallocene compound of orange solid form (racemic:meso=10:1) was obtained with the yield of 85% by filtering and vacuum drying the same.

$^1$H NMR (500 MHz, C$_6$D$_6$, 7.24 ppm): 1.19 (9H, s), 1.32 (3H, s), 1.48~1.86 (10H, m), 2.25 (6H, s), 3.37 (2H, t), 6.95 (2H, s), 7.13 (2H, t), 7.36 (2H, d), 7.43 (6H, t), 7.62 (4H, d), 7.67 (2H, d)

Step 3) Preparation of a Supported Catalyst

A metallocene catalyst supported on silica was prepared according to the same method as in Step 3 of Example, except that the metallocene compound ([(6-t-butoxyhexylmethylsilane-diyl)-bis(2-methyl-4-phenylindenyl)]zirconium dichloride) synthesized above was used.

Experimental Example

1) Homopolymerization of Propylene

After vacuum drying a 2 L stainless reactor at 65° C. and cooling the same, 1.5 mmol of triethylaluminum, 2 bar of hydrogen, and 770 g of propylene were sequentially added therein at room temperature. After stirring the mixture for 10 mins, 0.048 g of each of the metallocene catalysts prepared in Example and Comparative Example was dissolved in 20 mL of TMA-prescribed hexane and the solution was added to the reactor by nitrogen pressure. And then, after slowly elevating the temperature of the reactor to 70° C., the polymerization was carried out for 1 hr. After the reaction was terminated, unreacted propylene was vented out.

2) Random Polymerization of Propylene

After vacuum drying a 2 L stainless reactor at 65° C. and cooling the same, 1.5 mmol of triethylaluminum and 770 g of propylene were sequentially added therein at room temperature. After stirring the mixture for 10 mins, 0.048 g of each of the metallocene catalysts prepared in Example and Comparative Example was dissolved in 20 mL of TMA-prescribed hexane and the solution was added to the reactor by nitrogen pressure. And then, after slowly elevating the temperature of the reactor to 70° C. with adding 15 g of ethylene therein, the polymerization was carried out for 1 hr. After the reaction was terminated, unreacted propylene and ethylene were vented out.

3) Measuring Method of the Properties of the Polymer.

(1) Catalytic activity: the ratio of the weight of the produced polymer (kg PP) to the amount of the catalyst used (mmol and g of catalyst) was calculated, based on unit time (h).

(2) Melting point of polymer (Tm): melting point of polymer was measured by using a Differential Scanning calorimeter (DSC, Device Name: DSC 2920, Manufacturer: TA instrument). Specifically, after the polymer was heated to 220° C. and the temperature was maintained for 5 mins, the temperature was decreased to 20° C. again. And then, the temperature was increased again. At this time, the scanning speed of heating and cooling processes was respectively 10° C./min.

(3) Crystallization temperature of polymer (Tc): crystallization temperature was determined from the DSC curve obtained while decreasing the temperature with the same condition as the measurement on melting point by using the DSC.

(4) Stereoregularity of polymer (XS): the polymer was added to boiling o-xylene (ortho-xylene) and the amount of unextracted polymer after 1 hr was converted in a weight ratio (%).

Specifically, after preparing 200 mL of o-xylene in a flask, it was filtered with No. 4 filter paper of 200 mm. After drying an aluminum pan for 30 mins in an oven of 150° C., it was cooled in a desiccator and weighed. Subsequently, 100 mL of filtered o-xylene was collected and transferred to the aluminum pan by using a pipette, and all of o-xylene was evaporated by heating the pan to 145 to 150° C. After then, the aluminum pan was vacuum dried under the temperature of 100±5° C. and the pressure of 13.3 kPa for 1 hr. After cooling the aluminum pan in a desiccator, above processes were repeated twice. The blank test of o-xylene itself was finished within the weight error of 0.0002 g. And then, after drying the polymer obtained by the polymerization process of propylene (70° C., 13.3 kPa, 60 mins, vacuum dry), the polymer sample (2 g±0.0001 g) cooled in a desiccator was added in a 500 mL flask and 200 mL of o-xylene was added therein. The flask was connected to nitrogen and cooling water, and o-xylene was continuously refluxed for 1 hr by heating the flask. After cooling the flask below 100° C. by storing the same in the atmosphere, the insoluble material was precipitated by and shaking the flask and adding the same in a thermostatic bath (25±0.5° C.) for 30 mins. The resulted liquid in which precipitate was formed was repeatedly filtered with No. 4 filter paper of 200 mm until it became clean. 100 mL of the resulted liquid filtered clean was added in an aluminum pan that had been weighed after being dried at 150° C. for 30 mins and cooled in a desiccator, and o-xylene was evaporated by heating the aluminum pan to 145 to 150° C. When the evaporation was completed, the aluminum pan was vacuum dried under the temperature of 70±5° C. and the pressure of 13.3 kPa for 1 hr and cooled in a desiccator. The weight of the pan was measured within the error of 0.0002 g by repeating above processes twice.

After calculating the weight % (Xs) of the polymer dissolved in o-xylene by the following Calculation Equation 1, the weight ratio (=100–Xs) of the polymer that was not dissolved in o-xylene was obtained and it was defined as the stereoregularity (XI).

$$\text{Stereoregularity}(XI) = 100 - Xs \quad \text{[Calculation Equation 1]}$$

$$Xs = \left(\frac{Vbo}{Vb1} \times (W2 - W1) - \frac{Vbo}{Vb2} \times B\right)/Wo \times 100$$

In Calculation Equation 1, variations are as follows:

Xs=portion of the polymer dissolved in o-xylene (weight %)

Vb0=initial volume (mL) of o-xylene

Vb1=obtained volume of polymer solubilized in o-xylene (mL)

Vb2=obtained volume of o-xylene used in blank test (mL)

W2=sum (g) of the weights of the aluminium pan and the polymer left in the aluminum pan after evaporating o-xylene W1=weight of the aluminum pan (g)

W0=initial weight of the polymer (g)

B=average value (g) of the residue in the aluminium pan in blank test (5) Polydispersity index (PDI) and weight average molecular weight (Mw): weight average molecular weight (Mw) and number average molecular weight (Mn) of the polymer were measured by using a gel permeation chromatography (GPC, manufactured by Water Co.), and the polydispersity index (PDI) was calculated by dividing the weight average molecular weight by the number average molecular weight. At this time, the analyzing temperature was 160° C., the solvent was trichlorobenzene, and the molecular weight was standardized with polystyrene.

4) Results of the Properties of the Polymer Measured

The conditions of homo and random polymerization and the properties of polypropylene prepared by using each supported metallocene catalyst of Example and Comparative Example are listed in the following Table 1 (homopolymerization) and Table 2 (random polymerization).

TABLE 1

| | Example | Comparative Example |
|---|---|---|
| Liquid propylene (g) | 770 | 770 |
| Amount of supported catalyst (mg) | 45 | 60 |
| Polymerization temperature (° C.) | 70 | 70 |
| Hydrogen (ppm) | 337 | 337 |
| Activity (kg/gCat · hr) | 10.1 | 7.1 |
| Tm(° C.) | 149.9 | 148.7 |
| Tc(° C.) | 100.7 | 99.2 |
| Xs(%) | 0.70 | 0.75 |
| XI(%) | 99.30 | 99.25 |
| MFR | 7.0 | 9.8 |
| Mw | 289,000 | 262,000 |
| MWD | 2.7 | 2.9 |

TABLE 2

| | Example | Comparative Example |
|---|---|---|
| Liquid propylene (g) | 770 | 770 |
| Amount of supported catalyst (mg) | 45 | 45 |
| Polymerization temperature (° C.) | 70 | 70 |
| Ethylene (g) | 15 | 15 |
| Activity (kg/gCat · hr) | 12.6 | 9.6 |
| Tm(° C.) | 140.1 | 139.9 |
| Tc(° C.) | 87.3 | 90.3 |
| Xs(%) | 0.75 | 0.85 |
| XI(%) | 99.25 | 99.15 |
| MFR | 11.4 | 19.6 |

As shown in above Tables, Example in which the metallocene compound having the indenyl groups and a specific substituent at the bridge group according to the present invention was used in the form of a supported catalyst showed high activity enhancement effect in the preparation of polypropylene. Particularly, Example showed very excellent catalytic activities of 10.1 kg/gCat·hr in the homopolymerization and 12.6 kg/gCat·hr in the random polymerization, and the stereoregularity (XI), the characteristic of single site catalyst, of the prepared polymer was maintained at 99.25%-99.30%. Furthermore, the polypropylene polymer prepared in Example 1 showed very excellent characteristics such as the molecular weight distribution (MWD: Mw/Mn) of 2.7.

Furthermore, when the homopolypropylene is prepared at the same condition, the resin of which the molecular weight is increased by about 10% higher than Comparative Example can be prepared, and, particularly, the molecular weight was not decreased noticeably and the high molecular weight was maintained when the random polypropylene was prepared. Particularly, it is possible to prepare the polypropylene resin of lower molecular weight by increasing the amount of hydrogen provided thereto, and thus the polypropylene of wide molecular weight range can be prepared by the present invention. The metallocene compound prepared in Example can be used to prepare the polypropylene having higher molecular weight when it is polymerized at the same condition, because tert-butyl group of the same acts as an electron donor to the indenyl group and increases the cationic characteristic of zirconium, the center metal, and the activity in increased and the reaction speed is enhanced.

The invention claimed is:

1. A compound represented by the following structure:

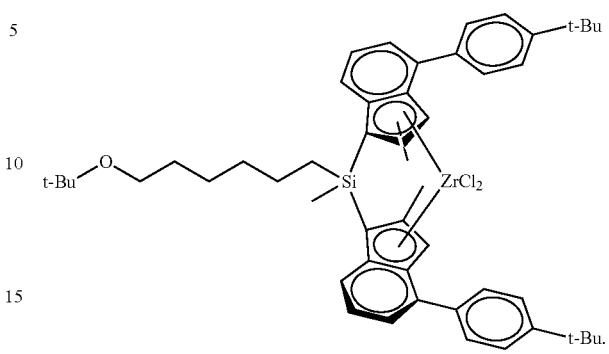

2. A catalyst for olefin polymerization, comprising the compound according to claim 1.

3. The catalyst for olefin polymerization according to claim 2, which is supported on at least one carrier selected from the group consisting of silica, silica-alumina and silica-magnesia.

4. A method for preparing polyolefin, comprising the step of polymerizing at least one olefinic monomer in the presence of the catalyst according to claim 2.

5. The method according to claim 4, wherein the olefinic monomer is at least one monomer selected from the group consisting of ethylene, propylene, 1-butene, 1-pentene, 1-hexene, 4-methyl-1-pentene, 1-octene, 1-decene, 1-dodecene, 1-tetradecene, 1-hexadecene, 1-octadecene, 1-eicosene, and a mixture thereof.

\* \* \* \* \*